United States Patent [19]

Miller

[11] Patent Number: 4,886,503

[45] Date of Patent: Dec. 12, 1989

[54] DISPOSABLE COVERED NEEDLE FOR SYRINGE

[75] Inventor: Ernest C. Miller, Jacksonville, Fla.

[73] Assignee: University Medical Center, Inc., Jacksonville, Fla.

[21] Appl. No.: 197,143

[22] Filed: May 23, 1988

[51] Int. Cl.⁴ ............................................. A61M 5/32
[52] U.S. Cl. ..................................... 604/192; 604/263
[58] Field of Search ................ 604/192, 187, 263, 198

[56] References Cited

U.S. PATENT DOCUMENTS 4,643,722  2/1987  Smith, Jr. ............................. 604/263
4,664,259  5/1987  Landis ............................. 604/192 X
4,747,836  5/1988  Luther ................................. 604/198

Primary Examiner—John D. Yasko
Attorney, Agent, or Firm—Arthur G. Yeager; Earl L. Tyner

[57] ABSTRACT

A covered needle assembly having a needle member and a cover member pivotably connected to each other, the cover member having a long narrow opening for the needle to pass through when the cover member is pivoted away from the needle when ready for use, the opening being covered by a rupturable plastic film which breaks when the cover is pivoted to expose the needle.

11 Claims, 3 Drawing Sheets

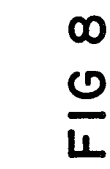
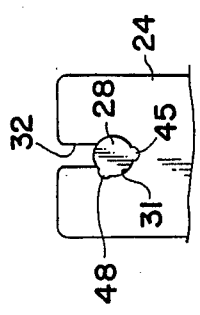
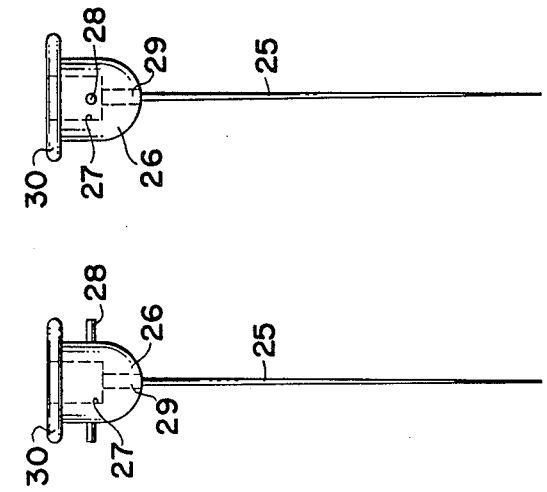
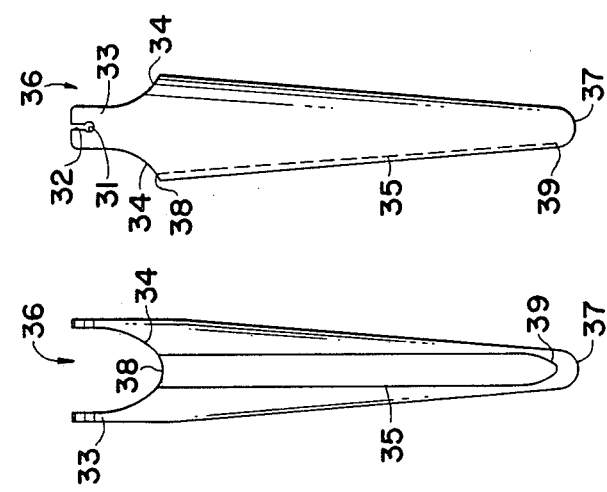
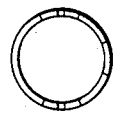
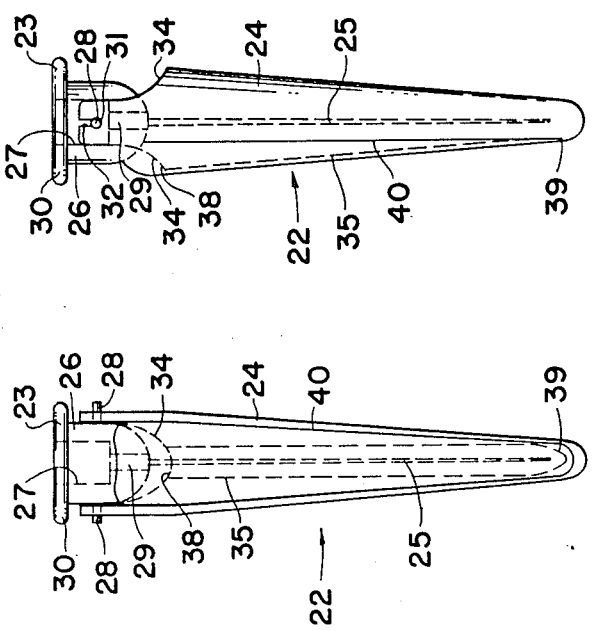
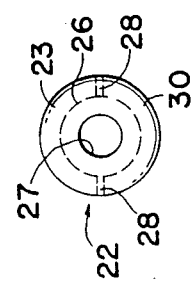

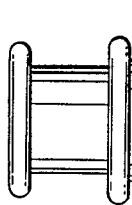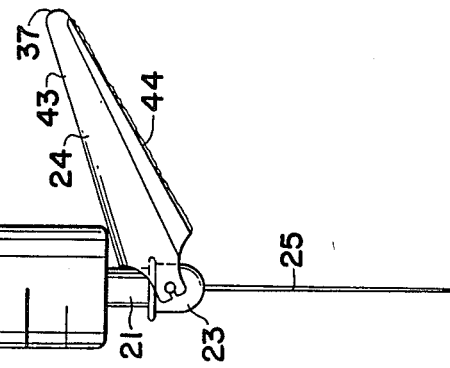
FIG 14
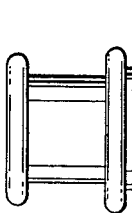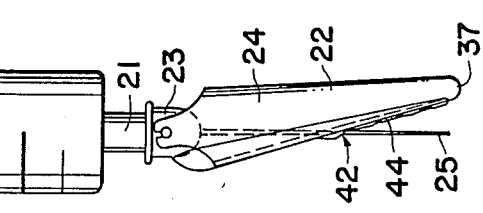
FIG 13
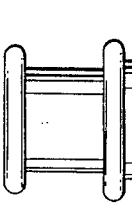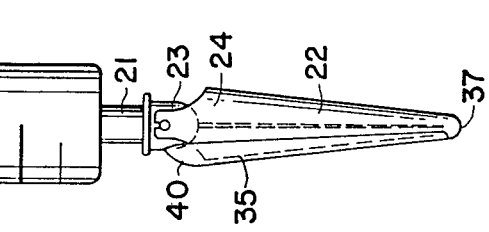
FIG 12
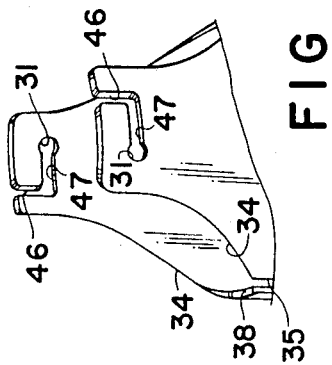
FIG 11
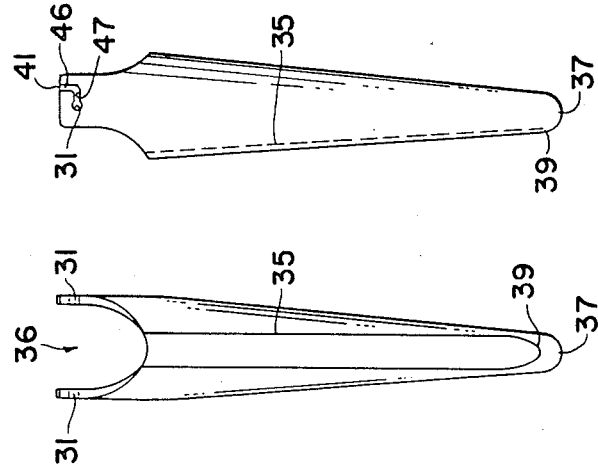
FIG 10
FIG 9

DISPOSABLE COVERED NEEDLE FOR SYRINGE

BACKGROUND OF THE INVENTION

A perennial problem with the use of hypodermic syringes in the past was the necessity to sterilize many syringes and needles while keeping the needle sharp. When the concept of disposable needles came into existence, the problems of sterilization were greatly reduced, and when disposable syringes were suggested most of the problems of sterilization and dull needles disappeared. Nevertheless, one problem remained and that involved the medical person using the syringe, who, through carelessness, frequently was stabbed by a used needle. Although this was serious when dealing with patients having certain infectious diseases the problem was greatly magnified when AIDS was recognized as a prevalent disease transmitted by intimate mixing of blood or other body fluids of an infected person with that of an uninfected person. The lack of a sure cure for AIDS has led to many safeguard procedures to protect medical personnel from inadvertent infection. Among the procedures are those relating to safe use of a syringe and needle for injections and/or the taking of blood samples.

Among the prior art devices for prevention of needle punctures are several types. U.S. Pat. No. 3,306,290 to Weltman discloses a spring biased needle which retracts completely inside the syringe body when not in use. The most simple device is that typified by U.S. Pat. No. 4,654,034 to Masters et al., which is merely a funnel entrance cover for a needle which is removed for use of the needle and replaced after use of the needle. Devices such as those of U.S. Pat. Nos. 4,610,667 and 4,623,336 to Pedicano et al. where the funnel-top cover has a hinged cap which is closed with the used needle inside so as to prevent inadvertent punctures by those handling the trash containing disposable needles. Finally, there is disclosed in U.S. Pat. No. 4,659,330 to Nelson et al, a needle guard attachable to a syringe to cover the needle, and to permit the cover to pivot away from the needle when being used, and to be returned to cover the needle after use. All of these devices have certain virtues, but none is as safe as the improved covered needle of the present invention.

It is an object of this invention to provide an improved disposable covered needle for a syringe. It is another object of this invention to provide an improved pivotable cover that virtually eliminates possibilities for inadvertent punctures by contaminated needles. Still other objects will become apparent from the more detailed description which follows.

SUMMARY OF THE INVENTION

This invention relates to a disposable covered needle for releasable attachment to a syringe having a short tubular inlet/exit pipe comprising a needle member and a cover member; said needle member including a hollow needle with a free end and an encased end, said encased end being embedded in a head having a socket to receive said inlet/exit pipe, a passageway connecting said socket to the hollow of said needle, and two pivot pins projecting outwardly on opposite sides of said head generally perpendicular to the hollow of said needle; and said cover member including a semirigid elongated sheath enclosing said needle and being pivotably attached to said pivot pins, a lengthwise narrow opening extending from the top of said cover to adjacent the tip of said needle and positioned to permit said needle to pass therethrough when said cover member is pivoted, and a rupturable plastic film covering said slot.

In a preferred embodiment of this invention the cover member is biased to remain in a fully pivoted or a nonpivoted position. In another embodiment the cover member must be twisted to lock it into operational position, so as to remove any possibility that the needle will inadvertently be exposed prior to intended use.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the covered needle assembly of this invention;

FIG. 2 is a side elevational view of the covered needle assembly of this invention;

FIG. 3 is a top plan view of the covered needle assembly of this invention;

FIG. 4 is a front elevational view of the cover member;

FIG. 5 is a side elevational view of the cover member;

FIG. 6 is a top plan view of the cover member;

FIG. 7 is a front elevational view of the needle member;

FIG. 8 is a side elevational view of the needle member;

FIG. 9 is a front elevational view of another embodiment of the cover member having a rotational lock arrangement;

FIG. 10 is a side elevational view of the cover member of FIG. 9;

FIG. 11 is an enlarged perspective view of the rotational lock arrangement of FIGS. 9 and 10;

FIG. 12 is a front elevational view of a syringe with the covered needle of this invention attached thereto;

FIG. 13 is a front elevational view of the syringe and covered needle of FIG. 12 illustrating the first pivoting of the cover member;

FIG. 14 is a front elevational view of the syringe and covered needle of FIGS. 12 and 13 illustrating the fully pivoted position of the cover;

FIG. 16 is an enlarged view of a pivot pin and the corresponding pivot hole to show the frictional means for holding the cover in its fully open or fully closed positions.

DETAILED DESCRIPTION OF THE INVENTION

Figure 15:
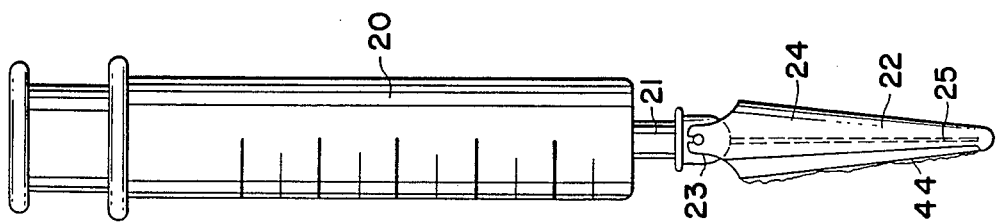
FIG. 15 is a front elevational view of the syringe and covered needle of FIGS. 12-15 after use and after returning the cover to its position of covering the needle.

The needle cover of this invention can best be understood by reference to FIGS. 1-11 of the attached drawings for the structural features and by reference to FIGS. 12-16 for the manner in which the covered needle is used.

In FIGS. 1-8 there are illustrated various views of the parts of the disposable covered needle of this invention. The entire assembly consists of two cooperating parts: needle member 23 and cover member 24. These two parts are joined together by means of pivot pins 28 and pivot holes or eyes 31 providing the opportunity for cover member 24 to pivot away from needle member 23 as may be seen in FIGS. 13 and 14, which will be described below.

Needle member 23 includes a cup-shaped head 26 having a recess 27 to receive the spout 21 of a medical syringe 20. This normally is a friction connection, but may include a short screw thread or other positive joining means. Hollow needle 25 has one end 29 embedded in head 26 with the other free end available for insertion into the body of a patient to perform an intravenous injection or to draw a sample of blood or other body fluid. Recess 27 communicates with the hollow of needle 25. The upper portion of head 26 is a flange 30 which provides a finger grip for pushing the covered needle assembly onto spout 21 of syringe 20. Head 26 also contains two pivot pins 28 extending out opposite sides thereof and adapted to suspend cover member 24 therefrom.

Cover member 24 is an elongated tubular structure having an upper open end 36 and a lower closed end 37. An opposite sides of open end 36 are arms 33, each containing a pivot eye 31 for attachment to a pivot pin 28 on needle member 23. Eye 31 is adjacent the top edge of arm 33 and is joined thereto by a narrow slot opening 32 which is somewhat narrower than the diameter of hole 31. Opening 32 serves the purpose of providing a way to assemble cover member 24 to needle member 23. Opening 32 will spring apart under a little pressure to allow pivot pin 28 to pass through to reach its proper position in hole 31, whereupon opening 32 will spring back to its normal position which will hold cover member 24 in place unless there is deliberate attempt to separate cover member 24 from needle member 23. If cover member 24 is made of a sufficiently flexible plastic, it may not be necessary to include opening 32. Assembly could then proceed by merely spreading arms 33 apart sufficiently to snap over pivot pins 28.

An elongated narrow opening 35 extends from the open top 36 to adjacent closed end 37. The upper end 38 of opening 35 is open and the lower end 39 of opening 35 is closed. Opening 35 is sufficiently long to allow needle 25 to be exposed when cover member 24 is pivoted away as in FIG. 14. The width of opening 35 need only be enough to allow needle 25 to swing through without touching cover member 24. The outside of opening 35 is a rupturable plastic film 40 which is heat sealed or adhesively attached to cover member 24. The position of film 40 is shown in FIGS. 1 and 2 in solid lines. Cover film 40 would be attached as a final step after joining cover member 24 to needle member 23. Preferably, film 40 would extend over the curved front 34 of cover member 24 and be sealed to cup-shaped head 26 of needle member 23 so as to provide protection against contamination when the covered needle assembly is attached to syringe 20.

In FIGS. 9-11 there is shown an alternative embodiment for cover member 24. In this design entrance opening 32, through which pivot pin 28 travels to reach hole 31 when assembling cover member 24 to needle member 23, is modified to an L-shaped slot 41 having a vertical leg 46 and a horizontal leg 47. The purpose of this arrangement is to provide additional safety against the possibility of needle member 23 inadvertently pivoting while the entire assembly 22 is being attached to syringe 20. The length of horizontal leg 47 is coordinated with the width of opening 35 so that if an inadvertent pivoting should occur while pushing pivot pin through vertical leg 46, needle 25 will not be aligned with opening 35 and will be prevented from pivoting outwardly. By twisting cover member 24 to move pivot pin 28 through horizontal leg 47 to hole 31, pivot pins 28 become properly aligned to allow needle 25 to pivot outwardly through opening 35. Other types of structures can be used to provide such a safeguard.

In FIGS. 12-15 there are shown the steps involved in using the device of this invention. In FIG. 12 the covered needle assembly 22 has been pushed onto spout 21 to a tight frictional fit. In FIG. 13, cover member 24 has been pivoted just enough for needle 25 to emerge as shown at 42 by rupturing film cover 40 leaving some remnants 44 of film cover 40. This movement can be done by one hand while the other holds syringe 20, but it also can be done by pushing closed end 37 of cover member 24 against a table top or the like to cause the pivoting without having a hand nearby that might get punctured by the emerging needle. In FIG. 14, cover member 24 has been pivoted as far away from needle 25 as possible so as to be ready for injection use. This movement of cover member 24 is merely a continuation of that which started in FIG. 13. It can be done by hand movement or a continuous pressure against a table or other solid object to move cover member 24. The entire length of film 40 is ripped open as indicated by torn film 44. In FIG. 15 the syringe has been used and cover member 24 has been returned to the original position of covering needle 25. This movement from the position of FIG. 14 to the position of FIG. 15 can be done by hand manipulation or by pushing end 37 against a table or other solid object.

Preferably, pivot pin 28 and hole 31 are fashioned so as to provide a bias toward maintaining cover member either in the fully open position of FIG. 14 or the fully closed position of FIGS. 12 and 15, to prevent cover member 24 from swinging indiscriminately. A typical procedure is that shown in FIG. 16 where pivot pin 28 and hole 31 are fashioned with corresponding protuberances on pin 28 and recesses on hole 31. The combination located at 45 may, for example maintain a bias toward keeping cover member 24 in a closed position, while the combination at 48 will bias cover 24 to remain in an open position. Such a combination of a small protuberance on pin 28 and a small recess in the perimeter of hole 31 results in an operational advantage whereby the operator of the syringe can feel the cover member 24 snap into place. Other temporary bias procedures can be employed.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to be secured by Letters Patent of the United States is:

1. A throw-away covered needle for releasable attachment to a syringe having a short tubular inlet/exit pipe said covered needle consisting essentially of a needle member and a cover member; said needle member including a hollow needle with a free end and an encased end, said encased end being embedded in a head having a socket to receive said inlet/exit pipe, a passageway connecting said socket to the hollow of said needle, and two pivot pins projecting outwardly on opposite sides of said head generally perpendicular to the hollow of said needle; and said cover member being a semirigid elongated sheath enclosing said needle member and having passageways therethrough for attachment to said pivot pins, a lengthwise narrow opening extending from the top of said cover member to adjacent said free end of said needle and positioned to permit said needle to pass therethrough when said cover member is pivoted, and a rupturable plastic film covering said slot.

2. The covered needle of claim 1 wherein said cover member is pivotably attached to said pivot pins by a pivot passageway for each said pin through said sheath pivotably fitting around said pin.

3. The covered needle of claim 2 wherein said sheath includes a slot from said pivot passageway to the nearest edge of said sheath and adapted to be temporarily spring apart to permit said pivot pins to pass therethrough to said pivot passageway.

4. The covered needle of claim 3 wherein said slot includes a vertical portion parallel to said needle joined to a horizontal portion perpendicular to said needle which terminates in said pivot passageway.

5. The covered needle of claim 1 wherein said pivot pins and the cooperating portions of said cover member include a small protuberance on said pin to cooperate with a small recess on said cover member positioned to bias said needle to lie along the lengthwise axis of said sheath.

6. The covered needle of claim 3 which has been sterilized and encased in a capsule package which is manually rupturable.

7. The covered needle of claim 1 wherein said rupturable plastic film is selected from the group consisting of polyolefin, polyamide, cellulose ester, polyester, polyvinyl esters and salts, and polyvinylidene esters and salts.

8. A safety covered needle for use on a medical syringe having a short tubular spout; said covered needle comprising a needle member and a cover member pivotally connected to said needle member; said needle member including cup-shaped head with an interior recess adapted to frictionally engage said spout, a hollow needle having a free end and having the other end embedded in said head, a passageway in said head joining said recess and said other end of said needle; and a pair of laterally extending pivot pins generally perpendicular to said needle; and said cover member being an elongated sheath having an upper open end and a lower closed end and a longitudinal axis corresponding to the hollow of said needle, a pair of eyes engageable with said pivot pins, an elongated narrow opening extending from an open end adjacent said eyes to a closed end adjacent said lower end of said sheath, and a ruptural plastic film covering all of said elongated narrow opening.

9. The covered needle of claim 8 wherein said sheath is a thin walled tubular plastic article and said eyes are holes through said thin wall with a narrow opening through said wall extending from said hole to a nearby edge of said sheath.

10. The covered wall of claim 8 wherein said narrow opening from said hole to the edge of said sheath is a short single linear opening.

11. The covered wall of claim 8 wherein said narrow opening from said hole to a nearby edge of said sheath is L-shaped with one leg of said L being substantially parallel with said axis and the other leg being substantially perpendicular to said axis.

* * * * *